(12) United States Patent
Lea et al.

(10) Patent No.: US 12,419,980 B2
(45) Date of Patent: Sep. 23, 2025

(54) DROPLET BANDPASS FILTER

(71) Applicant: Saban Ventures PTY Limited, Alexandria (AU)

(72) Inventors: Stephen Lea, Lane Cove West (AU); Phuong Tran, Lane Cove West (AU)

(73) Assignee: Saban Ventures PTY Limited, Lane Cove West (AU)

( * ) Notice: Subject to any disclaimer, the term of this patent is extended or adjusted under 35 U.S.C. 154(b) by 1052 days.

(21) Appl. No.: 17/253,417

(22) PCT Filed: Jun. 11, 2019

(86) PCT No.: PCT/AU2019/050597
§ 371 (c)(1),
(2) Date: Dec. 17, 2020

(87) PCT Pub. No.: WO2019/241828
PCT Pub. Date: Dec. 26, 2019

(65) Prior Publication Data
US 2021/0244841 A1    Aug. 12, 2021

(30) Foreign Application Priority Data

Jun. 21, 2018   (AU) .................................. 2018902224

(51) Int. Cl.
*A61L 2/22*    (2006.01)
*A61L 2/26*    (2006.01)
(Continued)

(52) U.S. Cl.
CPC .................. *A61L 2/22* (2013.01); *A61L 2/26* (2013.01); *B01D 45/04* (2013.01); *B01D 45/06* (2013.01);
(Continued)

(58) Field of Classification Search
None
See application file for complete search history.

(56) References Cited

U.S. PATENT DOCUMENTS 3,570,221 A    3/1971   Liver
5,916,640 A    6/1999   Liu et al.
(Continued)

FOREIGN PATENT DOCUMENTS

CN    105727330 A  *  7/2016
FR    2473315 A1      7/1981
(Continued)

OTHER PUBLICATIONS

CN105727330A_ENG (Espacenet machine translation of Zeng) (Year: 2016).*
(Continued)

*Primary Examiner* — Youngsul Jeong
(74) *Attorney, Agent, or Firm* — Stinson LLP

(57) ABSTRACT

A droplet bandpass filter and method of modifying droplet size distribution of a population of droplets suspended in a gas. Droplets suspended in a gas are flowed through a bandpass filter having a tortuous pathway which comprises at least one impactor region located at a position adjacent to a flow direction change. Larger droplets impact at the impactor region while smaller droplets remain suspended in the gas and flow in the first output direction. Other flow restrictors may advantageously be included in the tortuous pathway. The filter is particularly useful in delivering sterilant aerosols (e.g. peroxides) with reduced populations of large droplets.

22 Claims, 8 Drawing Sheets

(51) Int. Cl.
*B01D 45/04* (2006.01)
*B01D 45/06* (2006.01)
*B05B 12/00* (2018.01)
*A61L 101/02* (2006.01)
*A61L 101/36* (2006.01)

(52) U.S. Cl.
CPC ........... *B05B 12/00* (2013.01); *A61L 2101/02* (2020.08); *A61L 2101/36* (2020.08); *A61L 2202/15* (2013.01); *A61L 2202/24* (2013.01)

(56) References Cited

U.S. PATENT DOCUMENTS

| | | |
|---|---|---|
| 6,302,933 B1 | 10/2001 | Krause et al. |
| 6,513,727 B1 | 2/2003 | Jaser et al. |
| 2002/0098111 A1* | 7/2002 | Nguyen ................. A61L 2/208 422/28 |
| 2008/0110339 A1* | 5/2008 | Kwok ................. F24C 15/2035 95/79 |
| 2016/0184738 A1 | 6/2016 | Matsuura |

FOREIGN PATENT DOCUMENTS

| | | |
|---|---|---|
| JP | S60-220067 A | 11/1985 |
| JP | 64-032719 U | 3/1989 |
| JP | 5-45370 Y2 | 11/1993 |
| JP | 8-168706 A | 7/1996 |
| WO | 9416823 A1 | 8/1994 |

OTHER PUBLICATIONS

International Search Report and Written Opinion issued in PCT/AU2019/050597, dated Aug. 7, 2019, 11 pages.

* cited by examiner

DROPLET BANDPASS FILTER

REFERENCE TO RELATED APPLICATIONS

This application is a U.S. national stage application of International Patent Application No. PCT/AU2019/050597, filed Jun. 11, 2019, which claims the benefit of Australia Patent Application No. 2018902224, filed Jun. 21, 2018, the entire disclosures of which are incorporated herein by reference.

TECHNICAL FIELD

The invention relates to methods and apparatus for reducing the number of droplets of unwanted size from a mist having a distribution of droplet particle sizes. The invention is described primarily with reference to the filtration of a mist of a sterilant aerosol for provision to a sterilisation chamber for sterilising medical articles such as ultrasonic probes, although it will be appreciated that it is not limited to such a use and may be useful in other cases where control of droplet size is desirable.

BACKGROUND ART

Any discussion of the prior art throughout the specification should in no way be considered as an admission that such prior art is widely known or forms part of common general knowledge in the field.

Sterilizers are used in the medical, food and packaging industries to kill and thereby prevent the transmission of transmissible agents such as spores, fungi, and bacteria. A typical sterilizer creates a set of physical conditions in a sterilisation chamber that effectively kills nearly all of these transmissible agents.

Contacting articles in need of sterilisation with sterilant mists or aerosols is one known method of sterilisation. A conventional mist sterilisation apparatus has a sterilisation chamber with a mist inlet valve and a mist outlet valve, a mist generator (typically an ultrasonic nebulizer) in fluid communication with the chamber via the inlet valve and a fan upstream of, and in fluid communication with, the mist generator.

In use, an article requiring sterilisation is placed in the chamber, which is then sealed. The mist inlet valve is opened and the aerosol outlet valve is closed. The fan is engaged, which creates a gas stream through or the past the mist generator into the chamber. A passive vent in the sterilisation chamber allows for pressure equalization as required, to permit gas flow in and out of the sterilisation chamber. The mist generator, which contains the desired sterilant, is then activated, putting a large number of small sterilant droplets into gas stream. This mist of droplets is carried by the gas stream into the sterilisation chamber. The sterilant concentration in the mist stream can be adjusted by changing either the flow rate of the gas stream, the productivity of the mist generator, or the concentration of the liquid sterilant used.

The passive waste vent allows some flow to pass through it, allowing the sterilisation chamber to remain at approximately room pressure. This passive system may include a pathway for flow to the outside air past catalytic elements that react with the sterilant (which in many cases is a peroxy compound) and break the sterilant down into a safer chemistry suitable for disposal.

After a period of time, the fan and the mist generator are deactivated, and the air inlet valve is closed, hence completing the sterilant delivery phase. The exit valve is then opened and mist is actively removed, typically by way of a pump that pulls mist and vapour out of the sterilisation chamber at a high rate. The removal system may include a pathway for flow between the sterilisation chamber and outside air past catalytic elements that react with the sterilant and break the sterilant down into a safer chemistry suitable for disposal. The passive vent allows a source of fresh air to be drawn into the sterilisation chamber from the outside air.

It is generally desirable for the total sterilisation cycle time to be as short as possible. Short reprocessing durations increase the number of times the sterilised article can be used in a given period, which in turn increases the number of patients per day that can be treated. In the case where the article to be sterilised is a high-cost medical device, short cycle times can generate significant financial savings for a health care provider.

It is important to ensure that the sterilant mist droplets do not coalesce on the surface of the article and form droplets or regions of condensed liquids. Such regions of condensed liquid on the surface of the article to be sterilized are problematical in a number of ways.

It is highly desirable to have the article for sterilization in a dry state between each reapplication in a series of multiple re-applications of mist to ensure that the overall process achieves maximum efficiency. Layers of condensed liquids or droplets that build up on the surface contain potentially inactivated sterilant that prevents fresh sterilant mist from contacting the surface.

The formation of liquid layers on the surface of the article undergoing sterilization can also lead to multilayer B.E.T.-like absorption. Coalesced and absorbed droplets can be difficult to remove from the article at the end of the sterilisation process, effectively leaving it in a wet state. Residual sterilant left on the sterilised article can be harmful to operators and patients and as such are undesirable in a fully automated sterilisation device.

Residual sterilant on the surface of the sterilized article may be removed by washing, but this is an expensive feature to add to an automated sterilisation device and requires sterile water and fresh water supplies that cannot always be easily obtained. Alternatively, it is also undesirable to have staff hand-washing articles, as this requires the use of safety apparatus which can be expensive (such as fume hoods), can take up valuable time and space and moreover increases the risk of harmful sterilant coming into contact with an operator or patient. The addition of manual processes negates many of the advantages of automation.

A washing phase also requires a subsequent drying phase which adds considerably to apparatus turn-around times.

In general terms, larger droplets in a mist are more likely to condense on the surface of the article, thereby decreasing overall the efficacy of the sterilization process.

It is thus desirable to contact the article to be sterilized with a mist which has a reduced population of large droplet sizes. Mists can be generated from liquids in a number of ways, for example, by the application of ultrasonic energy or by the control of pressure, but regardless of the exact means of preparation, every mist contains a spread of particle size variations. This is illustrated in the idealised diagram in FIG. 1, where for example, the droplets range in particle size up to around 200 µm, with an average particle size of around 50 µm.

The inherent nature of the droplet size distribution in as-formed mists means that in order to prevent undesirable larger droplet sizes from contacting articles to be sterilized, treatment of the mist to is required so as to remove larger droplets and thereby preferentially allow smaller droplet sizes to contact the article to be sterilized.

It is an object of the present invention to overcome or ameliorate at least one of the disadvantages of the prior art, or to provide a useful alternative.

SUMMARY OF THE INVENTION

According to a first aspect, the invention provides a method of modifying droplet size distribution of a population of droplets suspended in a gas, the method comprising the step of flowing the population of droplets suspended in a gas through a tortuous pathway, wherein the tortuous pathway comprises at least one impactor region located at a position adjacent to a flow direction change from a first input flow direction to at least one first output flow direction, and wherein a first portion of the droplets impact and remain at the impactor region, and a second portion of the droplets remain suspended in the gas and flow in the at least one first output direction.

The tortuous flow pathway is constrained (and defined by) by a conduit, which may be of any cross section, such as a square, hexagonal, octagonal cross section, although most preferably the conduit is of a circular cross section. The droplets in the gas flow from one end of the conduit to the other.

The tortuous flow may in its simplest form be a bend in a conduit.

The tortuous flow may be a bifurcated flow, with one first input flow direction and two first output directions. The flow in each respective first output flow direction is preferably the same, that is, the bifurcation is preferably symmetrical. The output directions are preferably opposed.

Preferably, the droplet size distribution of particles in the first output flow is weighted towards smaller particle size than the droplet size distribution in the first input flow. That is, the output flow has an increased proportion of smaller particles, for instance, as may be shown by having a reduced MMAD in the output flow relative to the input flow. The MMAD of the particles in the output flow is less than the MMAD of the particles in the input flow.

The first input direction and first output direction are preferably orthogonal. The impactor region is ideally positioned to receive droplets following a path defined by a linear continuation of the first input direction.

The method may further include the step of passing the mist through one or more bends to cause an orthogonal flow direction change from an $n+1^{th}$ input flow direction to an $n+1^{th}$ output flow direction.

For example, it is preferred if the method further includes the step of passing the mist through a bend to cause an orthogonal flow direction change from a second input flow direction to a second output flow direction. In that case, the first output flow becomes the second input flow.

It is even more preferred if the method further includes the step of passing the mist through a bend to cause an orthogonal flow direction change from a third input flow direction to a third output flow direction. In that case, the second output flow becomes the third input flow.

One or more of the properties of the flow path, for example path diameter, may be selected to provide a mist having a predetermined droplet size profile.

Preferably. the predetermined droplet size profile excludes or substantially excludes droplets of or greater than a predetermined diameter, or the predetermined droplet size profile is MMAD (Mass Mean Aerodynamic Diameter) of droplets in the mist.

The method of the present invention may further include the step of passing the mist through an outlet of reduced diameter.

According to a second aspect the invention provides a droplet bandpass filter for a mist comprising a first inlet conduit, at least two first outlet conduits orthogonal to said first inlet conduit and an impactor region located at an end of the inlet conduit and positioned to receive a linear flow of droplets through the inlet conduit.

Preferably, the droplet bandpass filter further comprises n orthogonal bends, each bend having an $n+1^{th}$ inlet conduit and an $n+1^{th}$ outlet conduit.

For preference, the droplet bandpass filter further comprises an orthogonal bend having a second inlet conduit and a second outlet conduit. In that case, the first outlet conduit is in fluid communication with and defines the second inlet conduit.

More preferably, droplet bandpass filter further comprises an orthogonal bend having a third inlet and a third outlet conduit. In that case, the second outlet conduit is in fluid communication with and defines the third inlet conduit.

Preferably, each respective conduit is circular in cross section, and or of the same cross-sectional area.

The droplet bandpass filter of the present invention may also further comprise at a terminal position a flow restrictor. The flow restrictor may be a plate with an aperture, or alternatively it is a tube of narrowing dimension in the flow direction.

In yet a third aspect, the invention provides a sterilization apparatus including an ultrasonic nebulizer, a sterilization chamber, and a droplet bandpass filter according to the second aspect intermediate and in fluid communication with the ultrasonic nebulizer and the sterilization chamber to convey and filter droplets produced in the nebulizer to the chamber.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

References to "sterilisation" and "disinfection" as used herein may be used interchangeably and are also intended to include other levels of microbial reduction, including but not limited to sterilisation, high and low-level disinfection.

A "mist" as used herein is a system comprising a large population of discrete liquid particles of a relatively small size, having a population of sizes, suspended in a gas. The gas may be air. In the vicinity of the droplets, it is also possible that vapourised, i.e. gaseous material from the droplets is present. For instance, the mist may be particles of liquid hydrogen peroxide or peracetic acid in water suspended in air as a gas.

DESCRIPTION

The present invention provides methods and apparatus for removing larger sized droplets from a mist that are inherently produced when mists are created. As set out above, in the context of the present invention, which is sterilization, it is desirable to remove larger droplets from the mist as these can contribute to the formation of liquid layers on the surface of articles being disinfected. These liquid layers can prevent further active sterilant from contacting the surface and can leave articles wet following the sterilization procedure. Articles which are wet are not only perceived as undesirable, they can pose significant dangers to operators and patients if they contain active sterilant. This is particularly the case with peroxides which can cause great damage to mucosal membranes. Residual sterilant on the article can be removed by washing and or further drying, however that is undesirable as the length of the sterilization cycle is increased, increasing costs.

There are several methods available for the removal of specific populations of droplet sizes from misted solutions. These methods include scrubbers, cyclonic separation, physical filtration, and charge separation, for example. These approaches often create high resistance to droplet flow and are expensive to implement.

Physical methods, such as screening, may be effective in removing larger particles, but they tend to do so in a manner which also significantly reduces the number of smaller particles. This is undesirable from the point of view of wastage of sterilant, and the need for increased recycling or destruction of recovered unused sterilant.

Physical filtration means also present a high resistance to flow which is particularly undesirable. As well as being energetically unfavourable, medical sterilizers based upon misting technology typically use ultrasonic nebulizers of modest size and with modest power output. Similarly, the fans used to propel the mist are also relatively modest, so using high resistance filters is impractical.

Alternative processes such as cyclonic and charge separation processes are very complex and expensive.

As discussed above, in the present case, it is highly desirable for the process to produce a mist which has particles at the small end of the size distribution spectrum.

The present invention relies upon the change of direction or change in cross section of the flow path between the mist generator (typically, an ultrasonic nebulizer) and the target (a sterilization chamber which contains an article to be sterilized). Surprisingly, by selecting a specific configuration of tortuous pathway defined by a conduit, a predetermined effective particle cut off size can be set.

Figure 1:
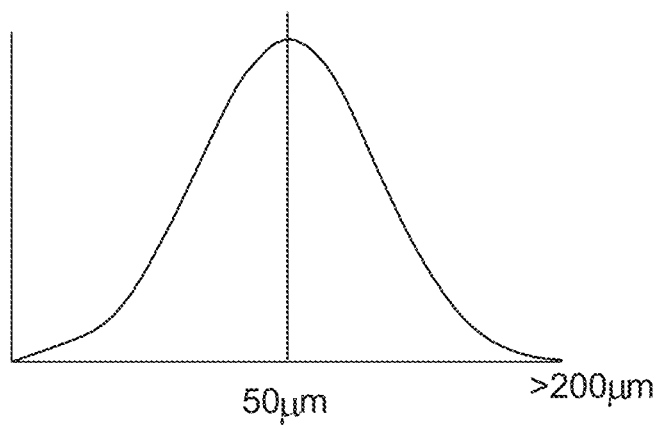
FIG. 1 shows droplet size distribution in a mist.
Figure 2:
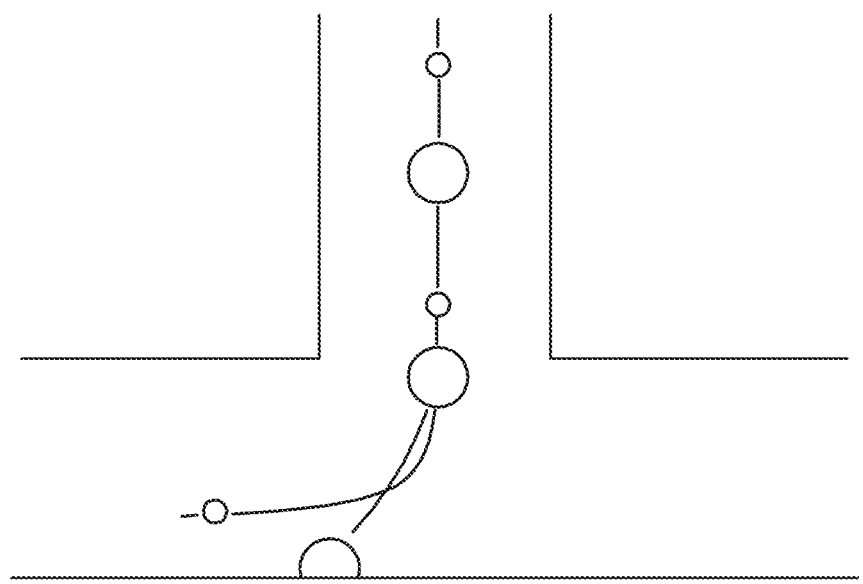
FIG. 2 shows separation technique based upon particle size.

The general principle employed in the present case is that the air flow into the low pass filter contains a mist that has a distribution of particles. As the mist flows around the turns in the pathway, those particles of large mass (and thus higher momentum) are unable to make a turn and will impact with the conduit walls surrounding the pathway and be removed from the airstream. The remainder of the droplets in the mist are able to flow around the turns without impacting the conduit walls and exit the conduit. The broad principal of operation is illustrated in FIG. 2, which shows the case for a single bend. Larger droplets are unable to turn in the necessary radius and collide with the opposing wall.

Figure 3:
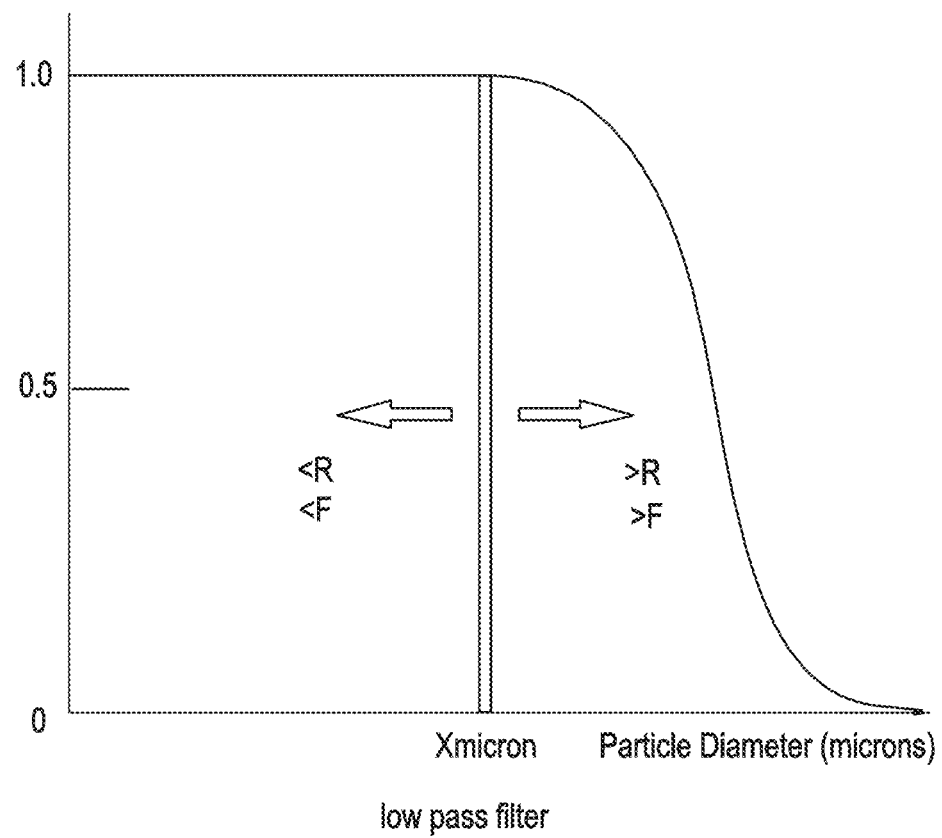
FIG. 3 shows the effect of the low pass filter of the present invention.

This change in direction results in an altered size distribution in the output stream relative to the inlet stream, and as FIG. 3 shows there is a reducing probability of larger particles passing through. Up to a certain size, there is a certainty that the particles will be able to make the turn and will pass through the filter. For particles above a certain size, there is a decreasing probability that the particles will not make the turn and will impact the impactor.

Interestingly, it is seen that this effect has a relatively steep point of inflexion in the sigmoid curve, meaning that the parameters can be tuned so as to not only restrict the passage of larger particles, but also to permit the passage of smaller particles.

The factors governing the particle cut off size are the flow rate and the nature of the restriction or tortuous path. As the flow rate of particles in a gas increases and/or the restriction increases (i.e. as the number of turns increases and/or the cross section of the flow path reduces in area), the maximum size of particles allowed through will be reduced. Similarly, as the flow rate of particles in a gas reduces or the restriction reduces (i.e. as the number of turns decreases and/or the cross section of the flow path increases in area) then the size of particles allowed through increases.

In general, in sterilizing apparatus, the flow rate into the chamber is fixed, based upon the operating parameters of the device and the amount of mist in total that can be generated. Although flow is one way to control the cut off size, in medical sterilizing devices, the flow cannot usually be dramatically altered as a required amount of sterilant needs to be delivered in a certain time, so restriction of the flow in some manner is the only viable method of control.

Figure 6:
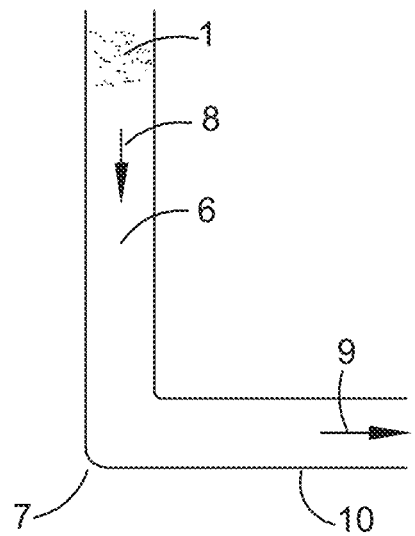
FIG. 6 shows a bend filter of the present invention.

The simplest embodiment of the invention is shown in FIG. 6. The size droplet size distribution of the mist can be modified by flowing the mist 1 in a first flow direction 8 through a tortuous pathway 6, wherein the tortuous pathway comprises an impactor region located adjacent bend 7, on the wall of conduit 10 where the flow direction changes from the first input flow direction 8 to a first exit flow direction 9. A portion of the droplets, corresponding to the larger sized droplets, impact the impactor region and are thus removed from the mist. A second portion of the droplets, corresponding to the smaller size droplets, plus a reduced fraction of the larger droplets, remain suspended in the gas and continue to flow in the first exit direction 9.

Figure 4:
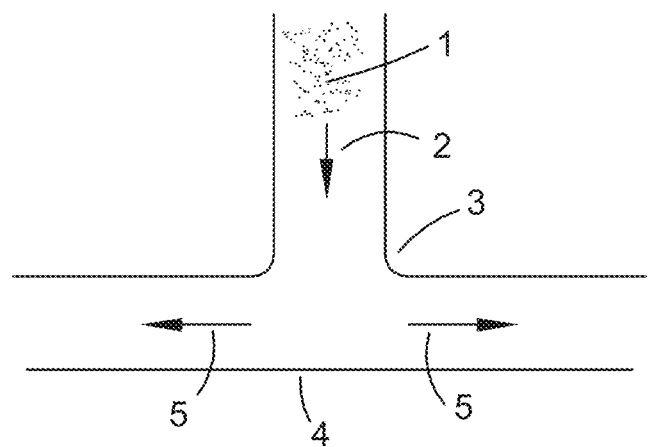
FIG. 4 shows a T-junction or impactor of the present invention.

A simple preferred embodiment of the invention is shown in FIG. 4. The size droplet size distribution of the mist can be modified by flowing the mist 1 in a first flow direction 2 through a tortuous pathway 3, wherein the tortuous pathway comprises an impactor region 4 located at a position where the flow direction changes from the first input flow direction 2 to a first exit flow direction 5. A portion of the droplets, corresponding to the larger sized droplets, impact the impactor region and are thus removed from the mist. A second portion of the droplets, corresponding to the smaller size droplets, plus a reduced fraction of the larger droplets, remain suspended in the gas and continue to flow in the first exit direction 5.

A plurality of first exit directions may be present. In the example shown, the tortuous pathway is in the form of a bifurcated "T" where the suspended droplets have two alternative, but equally probable, flow paths in the second direction 5.

The drawing shows a cross section of the tortuous pathway as being in one plane, although it is possible for a one or more of the bends to be out of plane-provided any second flow path is orthogonal to the first, this is acceptable.

Although the second pathway is shown to be at 90° to the first, a strictly orthogonal pathway is not absolutely necessary. The pathway can be at a greater or lesser angle if desired.

The relationship between the variables at the T junction or impactor is controlled by the following relationship:
Element 1: Impactor

| Parameters: | |
|---|---|
| Known Factors: | Values |
| $a_t/W$ = Input/Nozzle Diameter | 2.2 cm |
| $P_p$ = Particle Density | 1.45 g/cm$^3$ |
| $C_c$ = Slip Correction Factor | 1.012 |
| $\mu$ = Absolute Viscosity of the Fluid | $1.83 \times 10^{-4}$ dyn · s/cm$^2$ |
| With the following variables: | Values |
| $D_p$ = Particle Diameter | $1 \times 10^{-4}$ cm – $400 \times 10^{-4}$ cm |
| Stk – Stokes Number | 0 – 1 (if one then particle impacts, if laminar and <0.1 then zero impact) |

The Stokes number determines whether or not the particle impacts the impactor region. If the Stokes number is 1 or more, the particle will impact and not pass through the filter. Particles with a Stokes number of less than 0.1 are deemed to have a zero impact.

The relationship between the Stokes number and the Particle diameter is thus as follows:

$$Stk = P_p C_c D_p^2 U/9 \mu W$$

Which reduces to:

$$Stk = 17953 \times D_p^2$$

Then, looking at the behaviour of a sample various particle sizes in the mist, the results can be tabulated as follows:
Droplet Size Removal Past an Impactor:

| Particle Diameter ($D_p$) µm | Particle Diameter ($D_p$) cm | Stk | % Impact | % Pass |
|---|---|---|---|---|
| 1 | $1 \times 10^{-4}$ | 0.0002 | 0.02% | 99.98% |
| 10 | $10 \times 10^{-4}$ | 0.018 | 1.8% | 98.2% |
| 30 | $30 \times 10^{-4}$ | 0.159 | 15.9% | 84.1% |
| 50 | $50 \times 10^{-4}$ | 0.45 | 45% | 55% |
| 52.8 | $52.8 \times 10^{-4}$ | 0.5 | 50% | 50% |
| 64 | $64 \times 10^{-4}$ | 0.871 | 87.1% | 12.9% |
| 74.6 | $74.6 \times 10^{-4}$ | 1.0 | 100% | 0% |
| 80 | $80 \times 10^{-4}$ | 1.064 | 100% | 0% |
| 100 | $100 \times 10^{-4}$ | 1.73 | 100% | 0% |
| 200 | $200 \times 10^{-4}$ | 2.66 | 100% | 0% |

Figure 5:
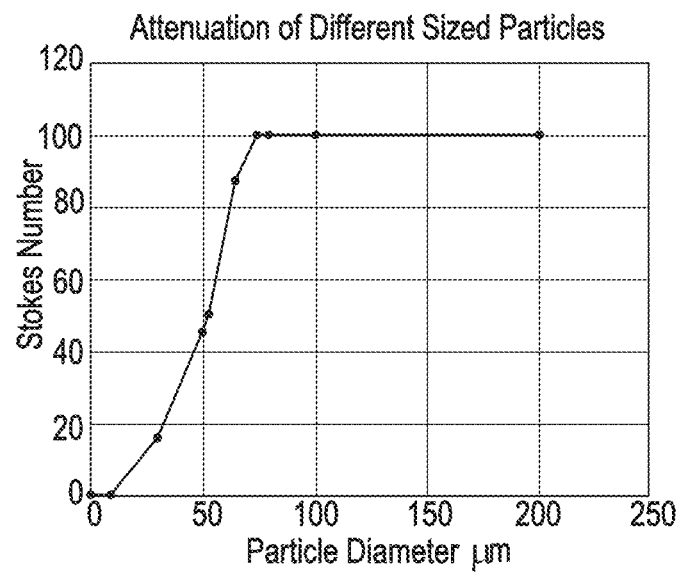
FIG. 5 shows droplet size attenuation caused by a T-junction or impactor of the present invention.

The results are graphed in FIG. 5. This shows that the T-junction or impactor described above, configured using the outlined design principals, attenuates all mist particles ~80 µm and above. Particles of 10 µm and below have very low chance of impaction making the first turn and will almost certainly be retained in the mist.

The process is advantageous because not only does it remove large unwanted particles from the mist it also allows smaller particles to pass unhindered. This is a significant advantage over restrictive methods, which remove not only large particles, but usually adversely affect the number of small particles. By allowing passage of small particles unhindered, the mist generated by the method of the present is done so in a very efficient manner, with minimal wastage of sterilant arising from particles of a useful size. Sterilant loss arising through removing larger, unwanted, particles is inevitable but an advantage of the present invention is that smaller particles of desirable size are preferentially retained in the mist, thereby minimising sterilant loss from removing particles of a desirable size.

Moreover, use of the above relationship allows a predetermined particle size to be selected and then delivered by the control of the various constructional elements. The control of the input diameter for example can be used to control the size of the cut off. Increasing the nozzle diameter for example decreases the Stokes number for a given particle size and makes it easier for the particles to pass through. If a specific cut off size is desired, it can be selected with the other parameters in mind and the conduit appropriately sized to ensure the Stokes number was at or below 1 as desired.

It has been found to be further advantageous to include additional elements to further enhance the selectivity of the bypass filter.

In particular, the invention includes one or more bends in series. The bends may be used alone or may receive the mist exiting the T-junction or impactor described above. The underlying premise in the case of the bends is not dissimilar to that of the T-junction or impactor. The mist flows around the bend and particles of a larger size have more momentum and are thus unable to make the turn without impacting the walls of the bend. The bend is generally formed of a conduit of uniform cross section. A single bend filter is shown in FIG. 6. Mist 1 flows into the conduit 6 with initial flow direction 8. The mist flows past bend 7 into an orthogonally disposed conduit 10 and exits with an exit direction 9 orthogonal to the original direction 8. Particles that are of sufficiently small size to make the turn at 7 will pass through, other particles will impact the conduit wall on the exit side 10 at or after bend 7.

Element 2: Bends

| Parameters: | |
|---|---|
| Known Factors: | Values |
| $a_t/W$ = Input/Nozzle Diameter | 2.2 cm |
| $P_p$ = Particle Density | 1.45 g/cm$^3$ |
| $C_c$ = Slip Correction Factor | 1.012 |
| $\mu$ = Absolute Viscosity of the Fluid | $1.83 \times 10^{-4}$ dyn · s/cm$^2$ |
| With the following variables: | Values |
| $D_p$ = Particle Diameter | $1 \times 10^{-4}$ cm – $400 \times 10^{-4}$ cm |

The losses in a bend are dictated by:

$$\eta = e^{-A \upsilon / Q}$$

Where:
 $\upsilon$ =Deposition Velocity
 $\eta$ =Fractional Penetration
 Q=Volume Flow Rate
 A=Deposition Area
 $\tau$ =Particle Relaxation Time
 F=area factor
Where:

$$\tau = P_p D_p^2 C_c / 18\mu$$

And:

$$\upsilon = \tau U_o^2 / R_B$$

And:

$$A = F(\pi^2 R_B a_t)$$

Put these together makes:

$$\ln \eta = -0.72 P_p D_p^2 Q / 18 a_t^3 \mu$$

$$\ln \eta = -52929 D_p^2 / a_t^3$$

This gives the relationship between the particle size and the fractional penetration (i.e. the likelihood of particles of that size passing through the bend.) Then, looking at the behaviour of a sample various particle sizes in the mist, the results can be tabulated as follows:

Droplet Size Removal Through a Single Bend:

| Particle Diameter ($D_p$) μm | Particle Diameter ($D_p$) cm | $\eta$ | % Pass | % Impact |
|---|---|---|---|---|
| 1 | 1 × 10$^{-4}$ | 0.996 | 99% | 1% |
| 5 | 10 × 10$^{-4}$ | 0.99 | 99% | 1% |
| 10 | 30 × 10$^{-4}$ | 0.961 | 96% | 4% |
| 20 | 20 × 10$^{-4}$ | 0.853 | 85% | 15% |
| 35 | 35 × 10$^{-4}$ | 0.614 | 61% | 39% |
| 50 | 50 × 10$^{-4}$ | 0.37 | 37% | 63% |
| 65 | 65 × 10$^{-4}$ | 0.186 | 19% | 81% |
| 80 | 80 × 10$^{-4}$ | 0.08 | 8% | 92% |
| 100 | 100 × 10$^{-4}$ | 0.019 | 2% | 98% |

Figure 7:
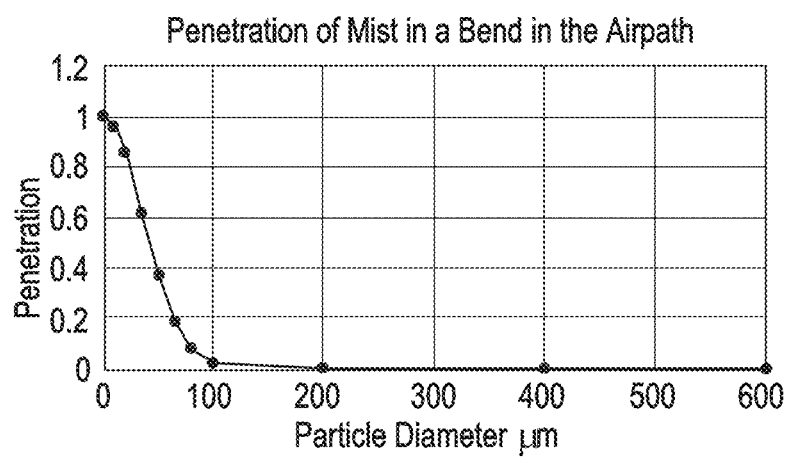
FIG. 7 shows droplet penetration around a single bend.

The result is shown graphically in FIG. 7, which shows that particles of diameter of 100 μm will deposit on the walls of a single bend, and that all diameters below that to 1 μm will be attenuated. The smaller particles, less than ten microns, will be attenuated less than 4% and particles of 5 microns or less will have a less than 1% attenuation.

Figure 8:
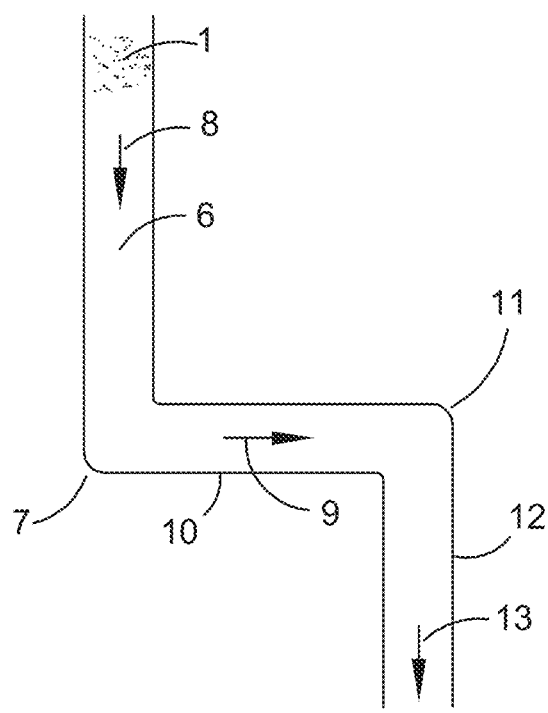
FIG. 8 shows a double bend filter of the present invention.

It is also possible to use a further bend, which may or may not be identical to the first. This is shown in FIG. 8. Mist 1 flows into the conduit 6 with initial flow direction 8. The mist flows past bend 7 into an orthogonally disposed conduit 10 and exits with an exit direction 9 orthogonal to the original direction 8. Particles that are of sufficiently small size to make the turn at 7 will pass through, other particles will impact the conduit wall on the exit side 10 at or after bend 7. The process is repeated at bend 11, where the exiting filtered mist from the first bend 7 becomes the feed mist for bend 10, which feeds into a further conduit 12 which discharges the double filtered mist at 13.

Figure 9:
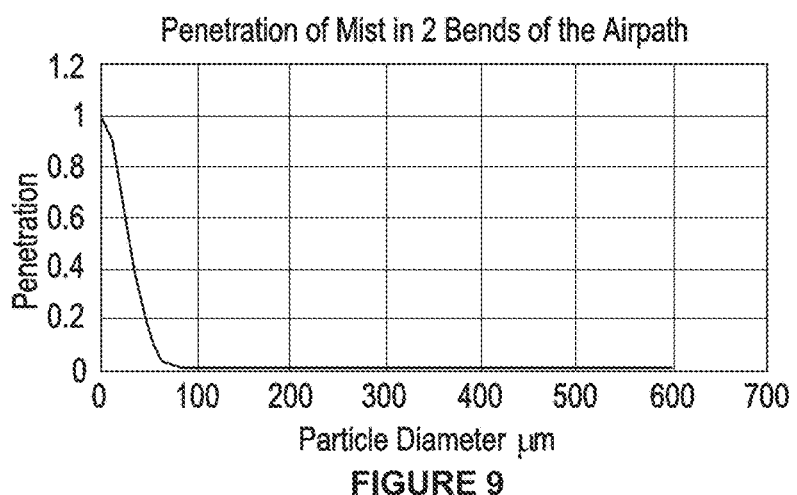
FIG. 9 shows droplet penetration around a double bend filter.
Figure 10:
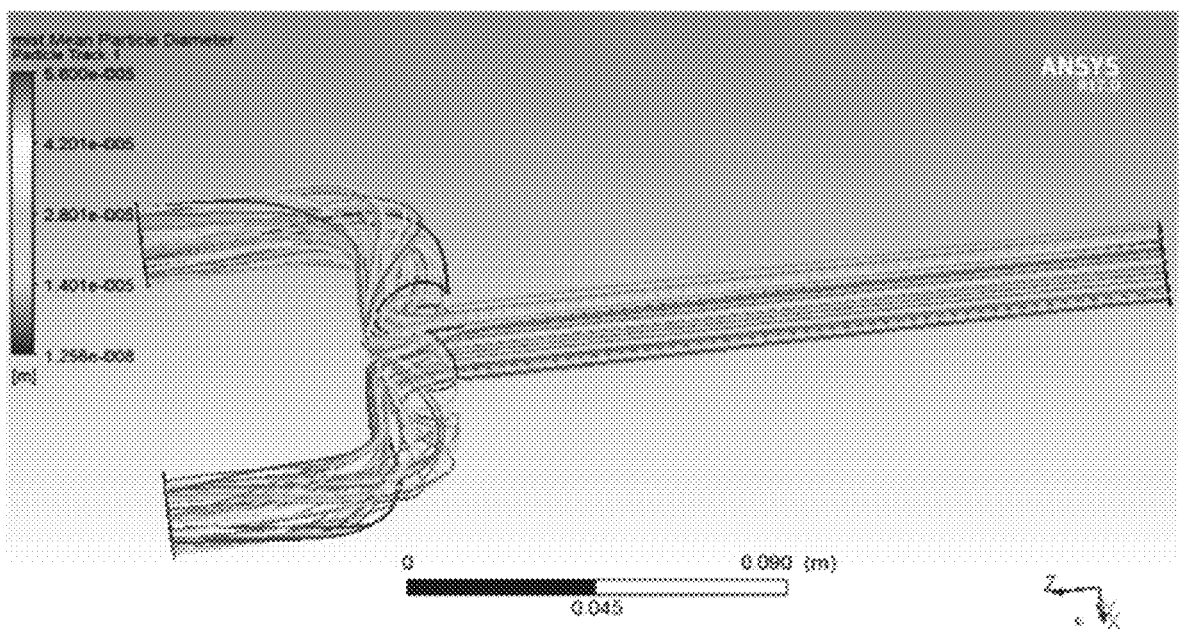
FIG. 10 shows a computer simulation of a T-junction or impactor in combination with a single bend.

In the case where the second bend is identical to the first, identical equations apply. The effect of two bends is thus multiplicative. The droplet bandpass for a second identical bend can thus be illustrated in FIG. 9. In this case, it can be seen that the slope of the transition region is becoming more vertical in nature, resulting a sharper cut-off and more thorough attenuation of larger particle sizes. Particle sizes of 5 μm or less have a 98% chance (0.99×0.99) chance of making both turns, whereas say a particle size of 100 μm, only 4 in every 10,000 particles will pass both turns and be delivered to the sterilization chamber.

Droplet Size Removal Through Two Bends:

| Particle Diameter ($D_p$) μm | Particle Diameter ($D_p$) cm | $\eta$ | % Pass | % Impact |
|---|---|---|---|---|
| 1 | 1 × 10$^{-4}$ | 0.996 | 99% | 1% |
| 5 | 10 × 10$^{-4}$ | 0.99 | 98% | 2% |
| 10 | 30 × 10$^{-4}$ | 0.961 | 92% | 8% |
| 20 | 20 × 10$^{-4}$ | 0.853 | 73% | 27% |
| 35 | 35 × 10$^{-4}$ | 0.614 | 38% | 62% |
| 50 | 50 × 10$^{-4}$ | 0.37 | 14% | 86% |
| 65 | 65 × 10$^{-4}$ | 0.186 | 3% | 97% |
| 80 | 80 × 10$^{-4}$ | 0.08 | 0% | 100% |
| 100 | 100 × 10$^{-4}$ | 0.019 | 0% | 100% |

The results could be repeated for any number of bends, although the size of the apparatus and the overall length of the mist pathway are competing priorities that need to be accommodated in reality.

It can thus be seen that the use of the tortuous pathway having a number of bends can sufficiently act as a cut off filter to effectively remove all particles of about 80 μm or greater (0.64% only passing) and indeed attenuate the mist such that the number of particles of 50 microns or greater is no more than a few percent of the total mist.

This relationship applies to any stable mist of droplets in a gas (aerosols). Sterilising mists include mists of peroxide compounds such as aqueous hydrogen peroxide or aqueous peracetic acid.

Element 3: Restrictions

The invention also includes a tortuous pathway having at its terminal end (i.e. at one or more endpoints of the pathway furthest from the droplet source) a restriction.

Figure 13:
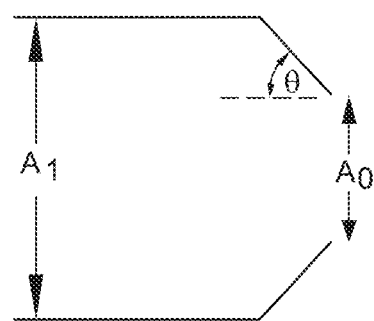
FIG. 13 shows the nature of the final restriction.
Figure 14:
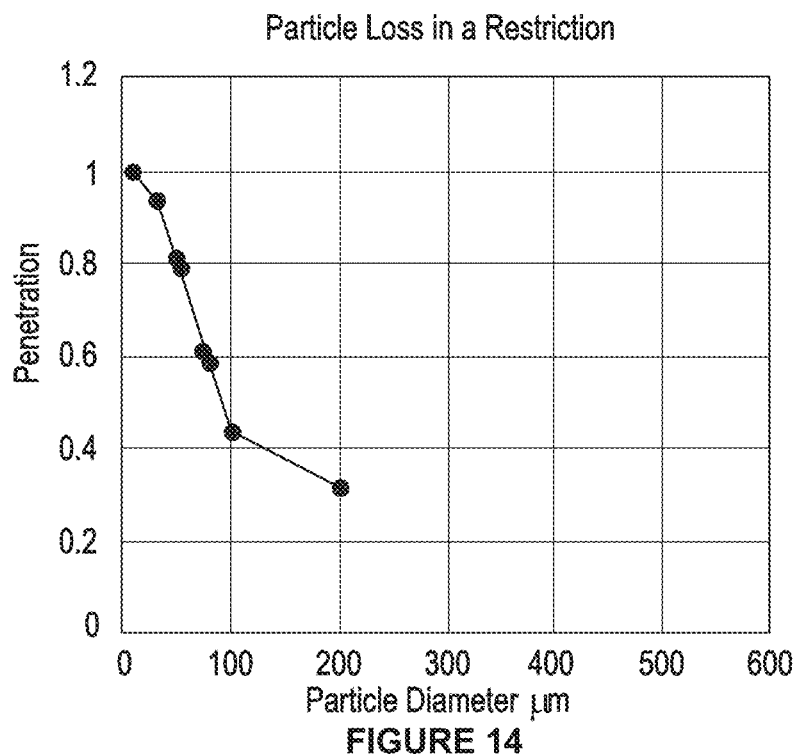
FIG. 14 shows droplet penetration through an example of a final restriction.
Figure 15:
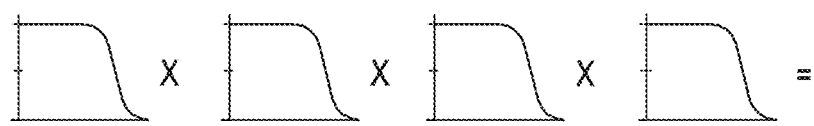
FIG. 15 illustrates the cumulative effect of filter elements in the present invention.
Figure 15:
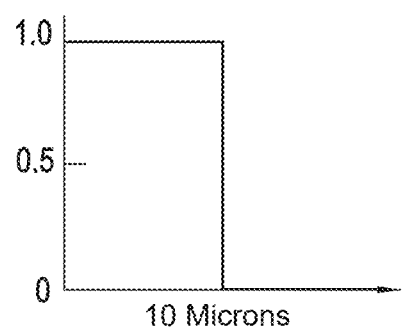

The nature of the restriction is shown in FIG. 13, which shows a cross section of the conduit in the region of the restrictor. The starting diameter is $A_1$, the final diameter is $A_0$ and the half angle is $\Theta$. The length of the restricted portion is ascertained from the starting and final diameters and the half angle. In the case where $\Theta$ equals zero, the tube has no restriction. In the case where $\Theta$ equals 90 degrees, the restriction is a plate with an aperture.

The restriction may be in the form of a plate or more preferably a gradual narrowing (tapering) of the cross section in the flow direction.

| Parameters | |
|---|---|
| Known Factors: | Values |
| $A_0/A_1$ = Difference of Diameters of constriction | $\Theta$ = half angle |
| $\Theta$ = half angle | 45° |
| With the following variables: | Values |
| $D_p$ = Particle Diameter | 1 × 10$^{-4}$ cm – 400 × 10$^{-4}$ cm |
| Stk – Stokes Number | 0 – 1 (if one then particle impacts, if laminar and <0.1 then zero impact) |

The losses in a restriction are given by the following formula:

$$\eta = 1 - 1/1 + (Stk(1-(A_0/A_1))/3.14 \exp(-0.01858))^{-1.24}$$

With the relationship between the Stokes number and the Particle diameter as previously set out:

$$Stk = P_p C_c D_p^2 U/9 \; \mu W$$

Which reduces to:

$$Stk = 17953 \times D_p^2$$

This gives the relationship between the particle size and the fractional penetration (i.e. the likelihood of particles of that size passing through the restriction.)

Then, looking at the behaviour of a sample various particle sizes in the mist, the results can be tabulated as follows:

Droplet Size Removal Through a Restrictor:

| Particle Diameter (Dp) μm | Particle Diameter (Dp) cm | η | % Pass | % Impact |
|---|---|---|---|---|
| 10 | 10 × 10 − 4 | 0.996 | 99% | 1% |
| 30 | 30 × 10 − 4 | 0.938 | 94% | 6% |
| 50 | 50 × 10 − 4 | 0.806 | 80% | 20% |
| 52.8 | 52 × 10 − 4 | 0.785 | 78% | 22% |
| 74.6 | 75 × 10 − 4 | 0.607 | 61% | 39% |
| 80 | 80 × 10 − 4 | 0.588 | 59% | 41% |
| 100 | 100 × 10 − 4 | 0.439 | 44% | 56% |
| 200 | 200 × 10 − 4 | 0.315 | 31% | 69% |

The results are given graphically in FIG. 14, which shows the effect of size restriction in the diameter of a circular cross section tube on droplets of various diameters.

It can be seen from the above that when a number of elements are added together, i.e. impactor, first bend, second bend and restrictor, the individual elements act in concert in a multiplicative manner to provide a filter with a sharply defined cut off region. The effects of each filter element act multiplicatively on the next filter. This is illustrated graphically in FIG. 15. The number of elements working in concert leads to a filter profile which approaches that of a bandpass filter. The filter of the present invention can be tuned, based on a suitable starting mist, by selecting the tube configuration in line with the principles above, to create a bandpass filter of any suitable cut off, for example, a 10 μm filter, By way of example only, looking at the tables above, it can be seen that a system having an impactor, two bends and a restrictor in the flow path will allow passage of close to 80% of 10 μm droplets, whilst allowing only about 6% of 50 μm droplets to exit the pathway. No droplets in the 100 μm range will reach the article to be sterilized.

Filtration to achieve a band pass filter that filters particles above 10 microns, is particularly desirable to achieve maximum and efficient microefficacy of the droplets, as well as reducing the time for the desired level of disinfection achieved, relative to the use of a mist with a broad range of droplet sizes. In enabling very efficient disinfection, the use of such droplets also results in a system which is safe for the user to handle and for subsequent patient contact.

Importantly, in the present case, the filters of the present invention operate to reduce the number of larger sized particles whist at the same time, do not greatly reduce the number of smaller particles. Thus, not only are the present bandpass filters highly effective, they are also efficient in permitting large numbers of desirable, small particles through.

The avoidance of larger droplets is also significant from an efficiency point of view, particularly in sterilization applications. Larger droplets not only cause problems with wetting as discussed above, they also contain significantly more sterilizing agent than smaller droplets. For example, a 100 μm particle carries 15 times more liquid than a 40 μm particle or 1000 times more liquid than a 10 μm particle. Removing large particles and recycling the peroxide can, over time, produce significant efficiencies. In addition, most sterilizers produce a sterilant residue that need to be treated before it can be vented into the atmosphere, for example, hydrogen peroxide usually requires catalytic destruction. By removing large unusable droplets from the system at a point where recycling is possible, an unnecessary load on such waste sterilant treatment systems is greatly reduced.

The system of the present invention having the T-intersection impactor and a single bend was subject to a detailed computer simulation and the results are shown in FIG. 10.

The simulation showed that when a mist comprising 5000 particles of 40 μm diameter was passed through the bandpass filter of the present invention (in the form of a T-impactor plus a single bend), around 1200 particles exit the system. A mist comprising 5000 particles of 10 μm size allows around 4500 particles to exit the system. Thus, it can be seen that a configuration having a single impactor and a single bend is far more restrictive for 40 μm particles than 10 μm particles, effectively acting as a filter even for such mid-range particles. The use of a second bend for example, would disproportionately reduce the 40 μm particles with minimal impact on the 10 μm particles, further enhancing the efficiency of the bandpass filter.

By the use of the equations presented herein, it is possible to devise a system in which a predetermined output can be obtained. For instance, knowing the target particle size and the mist flow rate, the diameter of the conduit defining the tortuous and/or restricted pathway can be adjusted to provide, for example, a specific cut off size, particularly with reference to the design of the impactor. Alternatively, other parameters of the populations of the droplets, such as the MMAD (mass median aerodynamic diameter) can be controlled.

A highly preferred system is shown in FIG. 11. Mist 1 enters in a first flow direction 2 through a tortuous pathway 3, wherein the tortuous pathway comprises an impactor region 4 located at a position where the flow direction changes from the first input flow direction 2 to a first exit flow direction 5.

A portion of the droplets, corresponding to the larger sized droplets, impact the impactor region and are thus removed from the mist. A second portion of the droplets, corresponding to the smaller size droplets, plus a reduced fraction of the larger droplets, remain suspended in the gas and continue to flow in the first exit direction 5.

The pathway also includes orthogonal bends 7 and 11 in series. The mist exiting the impactor at 5 feeds into bend 7 and then 11 and exits at 13. At bends 7 and 11, size restriction takes place in accordance with the above principle described for the double bends.

The invention has been described with reference to preferred embodiments, but it includes within its scope various configurations of T-Junctions and bends.

The invention maybe a simple T-Junction (impactor) alone, or it may be a single bend. The invention may be a T-Junction plus a bend on each of the bifurcated pathways exiting the T-junction, or it may have two bends, as illustrated above. The bends mat be the same or different.

The T junction need not be the first element encountered by the mist. The elements may be present in any order. For instance, the invention may comprise first a bend and then a T-junction or alternatively, a T-junction located between a leading bend and following bends on each of the bifurcated pathways exiting the T-junction, or it may be two bends immediately followed by a T-junction.

Figure 11:
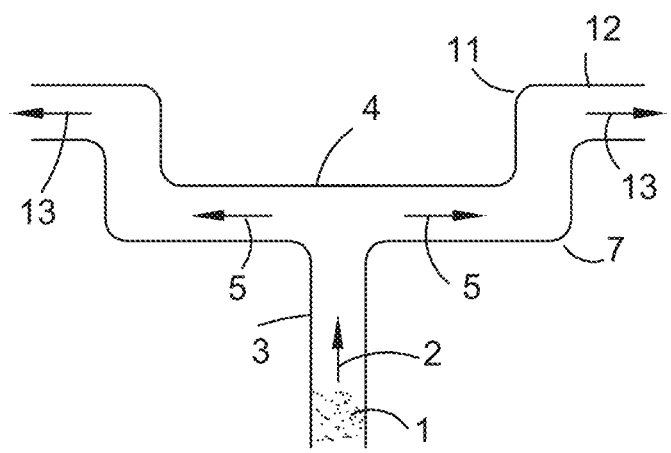
FIG. 11 shows a preferred embodiment of the present invention having a T-junction or impactor in addition to a double bend filter.
Figure 12:
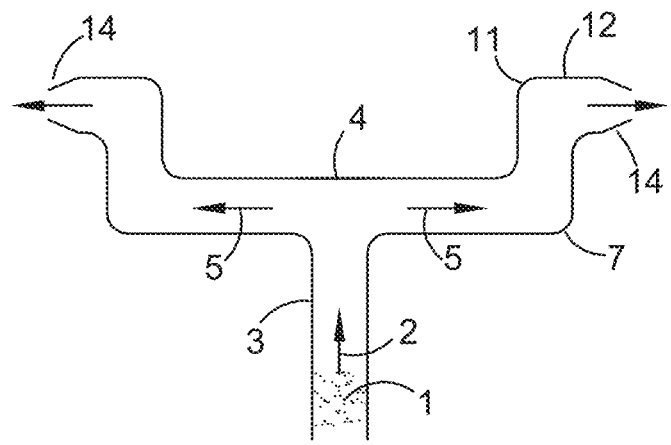
FIG. 12 shows a preferred embodiment of the present invention having a T-junction or impactor in addition to a double bend filter and a final restriction filter.

In addition, it has been found that adding a flow restriction 14 at the end of the tortuous pathway provides a further benefit in terms of the attenuation of larger particles which can be provided to the sterilization chamber. See FIG. 12, which shows the preferred embodiment of FIG. 11 equipped with terminal restrictions.

Figure 16:
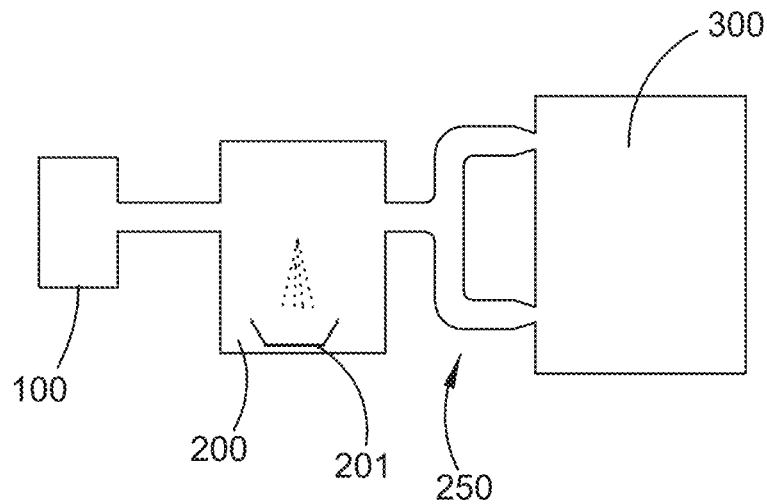
FIG. 16 shows a configuration of a tortuous filters of the present invention in a sterilizing apparatus.

The invention also encompasses the use of a T junction plus a restriction, or a bend and a restriction as well as other arrangements, such as a T-junction followed by a bend on each of the bifurcated pathways exiting the T-junction, and terminating in a restriction, or it may be a T-junction followed by a series of bends on each of the bifurcated pathways exiting the T-junction, and terminating in a restriction FIG. 16 shows a preferred embodiment of the invention in the context of a sterilization apparatus. Fan 100 is located upstream of, and in fluid communication with, nebulization chamber 200, which contains an ultrasonic nebulizer 201. Fan 100 blows mist generated in 200 via the tortuous filters of the present invention 250 into chamber 300 where it can sterilize articles contained therein. The tortuous filter comprises a T-junction and a bend filter on each bifurcation. A restriction may be located at or adjacent to where the filter 250 meets the chamber 300.

Figure 17:
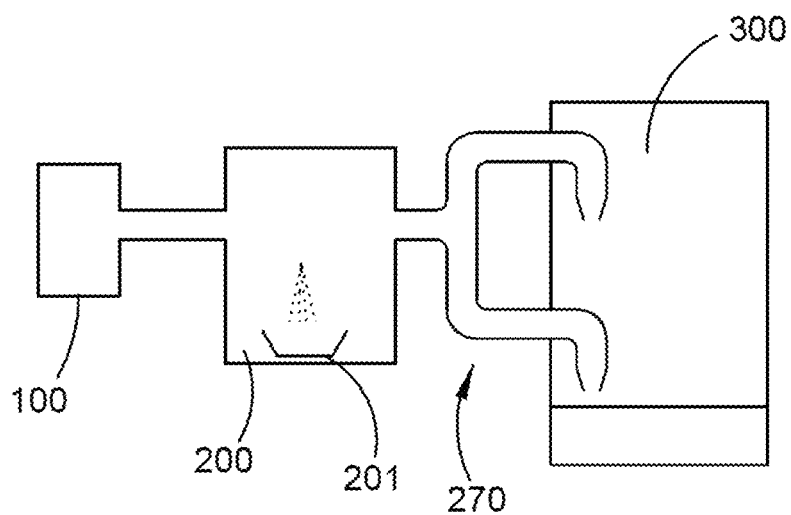
FIG. 17 shows an alternative configuration of a tortuous filters of the present invention in a sterilizing apparatus.

FIG. 17 shows an alternative preferred embodiment of the invention in the context of a sterilization apparatus. Fan 100 is located upstream of, and in fluid communication with, nebulization chamber 200, which contains an ultrasonic nebulizer 201. Fan 100 blows mist generated in 200 via the tortuous filters of the present invention 270 into chamber 300 where it can sterilize articles contained therein. The tortuous filter comprises a T-junction and a double bend filter on each bifurcation. The second bend in 270 is as shown is orthogonal and out of plane with the first bend although of course this is not necessary, and any suitable arrangement may be used to deliver the mist to chamber 300. A restriction may be located where the filter 270 meets the chamber 300.

In addition, testing of apparatus sterilized by the mist of the present invention appear dry compared to apparatus sterilised by conventional mists and in addition provide biological data that is consistent with a mist of smaller particles free from pooled and adsorbed liquids.

The invention claimed is:

1. A method of modifying a droplet size distribution of a population of droplets of a liquid sterilant suspended in a gas, the method comprising the steps of:
   flowing the population of droplets of the liquid sterilant suspended in the gas through a tortuous pathway, wherein the tortuous pathway comprises at least one impactor region located at a position adjacent to a flow direction change from a first input flow direction to a first output flow direction, wherein a first portion of the liquid droplets impact and are removed from the flowing gas at the at least one impactor region, and a second portion of the liquid droplets remain suspended in the gas and flow in the first output flow direction;
   recycling the sterilant from the first portion of the liquid droplets impacting and removed from the flowing gas at the at least one impactor region; and
   generating additional droplets of liquid sterilant suspended in the gas from the recycled sterilant.

2. The method according to claim 1, wherein the tortuous flow is a bifurcated flow, with the first input flow direction and two first output directions comprising the first output flow direction.

3. The method according to claim 2, wherein the flow in each respective two first output directions is the same.

4. The method according to claim 2, wherein the respective first output directions are opposed.

5. The method according to claim 1, wherein the droplet size distribution of particles in the first output flow is weighted towards smaller particle size than the droplet size distribution in the first input flow.

6. The method according to claim 1, wherein the first input flow direction and first output flow direction are orthogonal.

7. The method according to claim 1, wherein the at least one impactor region is positioned to receive droplets following a path defined by a linear continuation of the first input direction.

8. The method of claim 1, further including the step of passing the population of droplets through one or more bends to cause an orthogonal flow direction change from an $n+1^{th}$ input flow direction to an $n+1^{th}$ output flow direction.

9. The method of claim 8, further including the step of passing the population of droplets through one bend to cause the orthogonal flow direction change from a second input flow direction to a second output flow direction.

10. The method according to claim 9, wherein a first output flow from the first output flow direction becomes a second input flow in the second input flow direction.

11. The method according to claim 1, wherein a property of the flow in the first output flow direction is selected to provide a mist having a predetermined droplet size profile.

12. The method according to claim 1, wherein the droplets of liquid sterilant are suspended in air.

13. The method according to claim 1, wherein the droplets suspended in the gas are droplets of aqueous hydrogen peroxide or aqueous peracetic acid suspended in air.

14. The method according to claim 1, wherein the number of droplets 80 μm or greater in size is reduced to no more than 1%.

15. A sterilization apparatus, comprising:
   a mist generator for generating droplets of a liquid sterilant suspended in a gas; and
   a droplet bandpass filter comprising a first inlet conduit, at least two first outlet conduits orthogonal to said first inlet conduit and an impactor region located at an end of the first inlet conduit and positioned to receive a linear flow of the liquid sterilant droplets suspended in a gas from the mist generator through the first inlet conduit such that a first portion of the liquid droplets impact and are removed from the flowing gas at the impactor region,
   wherein the sterilization apparatus is configured to recycle sterilant from the first portion of the liquid droplets removed from the flowing gas at the impactor region to the mist generator to generate additional droplets of liquid sterilant suspended in the gas from the recycled sterilant.

16. The sterilization apparatus according to claim 15, further comprising n orthogonal bends, each bend having an $n+1^{th}$ inlet conduit and an $n+1^{th}$ outlet conduit.

17. The sterilization apparatus according to claim 15, further comprising an orthogonal bend having a second inlet conduit and a second outlet conduit.

18. The sterilization apparatus according to claim 17, wherein the first outlet conduit is in fluid communication with and defines the second inlet conduit.

19. The sterilization apparatus according to claim 15, wherein each respective conduit is of the same cross-sectional area.

20. The sterilization apparatus according to claim 15, further comprising at a terminal position a flow restrictor.

21. The sterilization apparatus according to claim 15, configured to provide a bandpass filter for removal of droplets above 10 microns in diameter.

22. The sterilization apparatus according to claim 15, which reduces the number of particles 80 μm or greater in size to no more than 1%.

* * * * *